United States Patent

Pelosi, Jr.

[11] 4,067,888
[45] Jan. 10, 1978

[54] 5-(4-CHLOROPHENYL)-N-(2-PROPYNYL)-FURFURYLAMINES

[75] Inventor: Stanford S. Pelosi, Jr., Norwich, N.Y.

[73] Assignee: Morton-Norwich Products, Inc., Norwich, N.Y.

[21] Appl. No.: 769,319

[22] Filed: Feb. 17, 1977

[51] Int. Cl.² ........................................... C07D 307/52
[52] U.S. Cl. ................................. 260/347.7; 424/285
[58] Field of Search ...................................... 260/347.7

[56] References Cited

U.S. PATENT DOCUMENTS 2,105,808   1/1938   Cramer ........................ 260/347.7 X
3,210,361  10/1965   Humber ....................... 260/347.7 X
3,211,741  10/1965   Martin et al. ................. 260/347.7 X Primary Examiner—Richard L. Raymond
Attorney, Agent, or Firm—Anthony J. Franze

[57] ABSTRACT

Certain 5-(4-chlorophenyl)-N-(2-propynyl)furfurylamines of the formula:

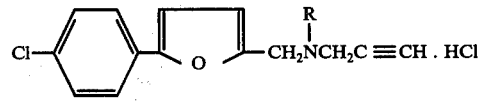

wherein R represents hydrogen or methyl are effective anti-inflammatory agents.

3 Claims, No Drawings

5-(4-CHLOROPHENYL)-N-(2-PROPYNYL)FURFURYLAMINES

This invention relates to chemical compounds. More particularly this invention relates to certain 5-(4-chlorophenyl)-N-(2-propynyl)furfurylamines of the formula:

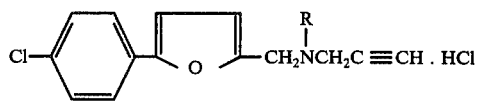

wherein R represents hydrogen or methyl and a method for their preparation. The compounds of this invention possess pharmacologic activity. They are particularly useful as anti-inflammatory agents as evidenced by their ability to inhibit edema induced in rats by the administration of carrageenin. Thus, when administered at a dose of 300 mg/kg suspended in a vehicle such as aqueous methylcellulose per os to rats receiving carrageenin, edema associated with that substance is inhibited by 58–60% [Winter et al. P.S.E.B.M. 111:544 (1962)].

The compounds of this invention are readily prepared. Currently it is preferred to prepare the compounds wherein R is hydrogen by reacting 5-(4-chlorophenyl)furfural with monopropargylamine in the presence of a solvent such as methanol followed by treatment with sodium borohydride. When R represents methyl, it is currently preferred to react 5-(4-chlorophenyl)furfuryl chloride with N-methylpropargylamine in the presence of a solvent such as benzene.

In order that this invention may be fully available to and understood by those skilled in the art, the methods now preferred for making them are described.

EXAMPLE I

5-(4-Chlorophenyl)-N-(2-propynyl)furfurylamine hydrochloride

A mixture of 8.3 g (0.04 mole) of 5-(p-chlorophenyl)furfural and 2.2 g (0.04 mole) of mono-propargylamine in 50 ml of MeOH was stirred at room temperature for 0.5 hr, heated under reflux for 1 hr and cooled to 15°. Sodium borohydride (1.5 g, 0.04 mole) was added in portions over 0.5 hr at 15°–20°. The solution was stirred at room temperature for 3 hrs, allowed to stand overnight, and evaporated to dryness on a rotary evaporator. The residue was partitioned between $CH_2Cl_2$ and $H_2O$, and the layers were separated. The aqueous layer was extracted with $CH_2Cl_2$ and the combined $CH_2Cl_2$ layers were dried over $MgSO_4$. The solvent was removed on a rotary evaporator to give 9 g of solid which was dissolved in 130 ml of anhydrous ether and treated with 20 ml of etheral HCl. The yellow solid which was deposited was collected by filtration to give 9 g (80%) of product. Recrystallization from $CH_3CN$ gave an analytical sample, m.p. 179°–183°.

Anal. Calcd. for $C_{14}H_{12}NOCl\cdot HCl$: C, 59.59; H, 4.64; N, 4.96. Found: C, 59.21; H, 4.61; N, 4.98.

EXAMPLE II

5-(4-Chlorophenyl)-N-methyl-N-(2-propynyl)furfurylamine Hydrochloride

N-Methylpropargylamine (25 g, 0.38 mole) was added to a solution of 5-(p-chlorophenyl)furfuryl chloride (40 g, 0.22 mole) in 400 ml of benzene. The solution was heated under reflux with stirring for 5 hrs and allowed to stand overnight. The solid N-methylpropargylamine hydrochloride (20 g, 100%) was collected by filtration and discarded. The filtrate was washed with 5% aq. $NaHCO_3$ and water and was dried over $MgSO_4$. The solvent was removed on a rotary evaporator to give 52 g of a residual oil. A solution of the oil in 700 ml of EtOAc was treated with 50 ml of etheral HCl. Anhydrous ether (700 ml) was added, and the mixture was cooled at 0° overnight. The solid was collected by filtration and was dried in a vacuum desiccator to give 32 g (49%) of product. Drying overnight under reduced pressure at the temperature of refluxing $CHCl_3$ gave an analytical sample, m.p. 180°–183°.

Anal. Calcd. for $C_{15}H_{14}ClNO\cdot HCl$: C, 60.80; H, 5.10; N, 4.73. Found: C, 60.45; H, 5.18; N, 4.87.

What is claimed is:

1. A compound of the formula:

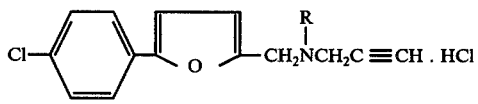

wherein R represents hydrogen or methyl.

2. The compound 5-(4-chlorophenyl)-N-(2-propynyl)furfurylamine hydrochloride.

3. The compound 5-(4-chlorophenyl)-N-methyl-N-(2-propynyl)furfurylamine hydrochloride.

* * * * *